United States Patent [19]

Lee et al.

[11] Patent Number: 5,693,501

[45] Date of Patent: Dec. 2, 1997

[54] **COMPOUNDS AND METHODS TO DETERMINE PRESENCE OF *HISTOPLASMA CAPSULATUM***

[75] Inventors: Chao-Hung Lee; Bingdong Jiang, both of Indianapolis, Ind.

[73] Assignee: Indiana University Advanced Research & Technology Institute, Bloomington, Ind.

[21] Appl. No.: 400,580

[22] Filed: Mar. 8, 1995

[51] Int. Cl.$^6$ .................. C12P 19/34; C12Q 1/68; C07H 21/04; C07H 21/02

[52] U.S. Cl. .................. 435/91.2; 435/6; 536/24.3; 536/24.33; 536/23.1

[58] Field of Search .................. 536/24.3–24.33, 536/23.1; 435/6, 91.2

[56] References Cited

U.S. PATENT DOCUMENTS 5,352,579  10/1994  Millman .................. 435/6

OTHER PUBLICATIONS

Tisserat et al. Phytopathology 84:478–482, 1994.
LoBuglio et al. J. of Clinical Microbiology 33: 85–89, 1995.
O'Gorman et al. Canadian J. of Botany 72: 342–346, 1994.
Huffman et al. Experimental Mycology 16: 316–319, 1992.

*Primary Examiner*—W. Gary Jones
*Assistant Examiner*—Dianne Rees
*Attorney, Agent, or Firm*—Kristine H. Johnson

[57] ABSTRACT

The present invention combines detection and identification of *H. capsulatum* in one step, eliminating the need to use DNA probes to react with PCR products in order to distinguish different types of fungi. The purpose of the invention is to provide compounds and methods to directly and specifically identify *H. capsulatum* in clinical specimens. Specifically, we provide a unique nucleotide sequence from the rRNA gene internal transcribed spacer region I (ITSI) of *H. capsulatum* and a PCR method which amplifies the unique sequence of *H. capsulatum*.

13 Claims, No Drawings

COMPOUNDS AND METHODS TO DETERMINE PRESENCE OF *HISTOPLASMA CAPSULATUM*

BACKGROUND OF THE INVENTION

The present invention relates to diagnosis of *Histoplasma capsulatum* infections via a polymerase chain reaction (PCR) method for direct detection and identification of Internal Transcribed Spacer Region I (ITSI) of nuclear ribosomal RNA Genes of *Histoplasma capsulatum* (*H. capsulatum*) in clinical specimens. The purpose of the invention is to expediate clinical diagnosis of *H. capsulatum* infections.

*H. capsulatum* is a fungal patbogen which causes histoplasmosis, a mycosis with an array of manifestations. Some persons may experience mild flu-like symptoms or pneumonia, while others, especially the immune-suppressed, can develop lesions of the brain, intestine, adrenal gland, heart, spleen, lymph nodes, liver and bone marrow. *H. capsulatum* is attributed to 500,000 infections per year, with several thousand resulting in hospitalizations. A small number of these cases result in death.

The fungus is prevalent in humid river basins; a well-documented region of *H. capsulatum* prevalence in the U.S. is the Ohio River valley. *H. capsulatum* is usually dimorphic, meaning that it is a white or brown hair-like mycelium when grown below 35 degrees Celsius and is a white, smooth colony when grown on blood agar at 37 degrees Celsius.

The commonly-used procedures for diagnosing *H. capsulatum* infection are: 1) detection of *H. capsulatum* antigen in clinical specimens such as bronchoalveolar savage (BAL), serum, urine, or other body fluids, generally in accordance with Wheat, J., et al., *New Eng. J. Med.*, 314:83–88. (1986); 2) detection of antibodies in serum, generally in accordance with Wheat J., et al., *Ann. Int. Med.*, 97:680–685 (1982); 3) detection of *H. capsulatum* organisms by culture; 4) detection of *H. capsulatum* organisms by microscopy in conjunction with the methods above. Culture of the fungus is the final proof of positive diagnosis because of the high possibility of producing false positive and false negative results by other methods; however, culture is a very slow process. Proving dimorphism can take weeks, due to the difficulty in culturing the organism.

As of 1992, another method became available for diagnosis in Bowman, B. H., *Clinical Immunology Newsletter* 12:65–69 (1992). In that publication, detection and identification of *H. capsulatum* by PCR were achieved indirectly. A portion of the 18S rRNA gene was amplified by using a pair of oligonucleotide primers capable of amplifying all fungi. The amplified PCR products were then reacted with probes specific for a certain fungus such as *H. capsulatum*, *Blastomyces dermatitidis*, *Coccidioides immitis*, *Trichophyton rubrum*, or *Candida albicans*. If a PCR product reacted with the *Candida albicans* probe, the sample would contain *Candida albicans*. However, the probe (Bd/Hc) suggested for detection of *H. capsulatum* also reacted with *B. dermatitidis* and, therefore, another probe (Bd) that reacts only with *B. dermatidis* was necessary to distinguish *H. capsulatum* from *B. dermatitidis*. By this method, a PCR product which reacted with both the Bd and the Bd/Hc probes would indicate the presence of *B. dermatitidis*, whereas a PCR product which reacts with only the Bd/Hc probe would indicate the presence of *H. capsulatum*. This method is extremely cumbersome to perform and is very labor-intensive and time-consuming.

SUMMARY OF THE INVENTION

The present invention combines detection and identification of *H. capsulatum* in one step, eliminating the need to use DNA probes to react with PCR products in order to distinguish different types of fungi. The purpose of the invention is to provide compounds and methods to directly and specifically identify *H. capsulatum* in clinical specimens. Specifically, we provide a unique nucleotide sequence from internal transcribed spacer region I (ITSI) of the rRNA genes of *H. capsulatum* and a PCR method which amplifies the unique sequence of *H. capsulatum*.

The present invention can produce a final result within 3 days and makes it possible to directly detect *H. capsulatum* in clinical specimens and differentiate it from other fungi, including *Blastomyces dermatitidis*.

When used in this description, the term "patient" is intended to mean any animal susceptible to infection by *H. capsulatum* including, but not limited to, humans and livestock.

Other features of the present invention will be apparent from the following detailed description of the preferred embodiment.

BRIEF DESCRIPTION OF THE SEQUENCE LISTING

The invention will be further described in conjunction with the accompanying sequence listing, in which:

SEQ ID NO. 1 is the double-stranded DNA sequence of the internal transcribed spacer region 1 of rRNA genes from *H. capsulatum;*

SEQ ID NO. 2 is the single-stranded 5' to 3' DNA sequence of the internal transcribed spacer region 1 of rRNA genes from *H. capsulatum;*

SEQ ID NO. 3 is the single-stranded 3' to 5' DNA sequence of the internal transcribed spacer region 1 of rRNA genes from *H. capsulatum;*

SEQ ID NO. 4 is a 189 base pair fragment of SEQ ID NO. 1;

SEQ ID NO. 5 is a 189 base fragment of SEQ ID NO. 2;

SEQ ID NO. 6 is a 189 base fragment of SEQ ID NO. 3;

SEQ ID NO. 7 is a 22 base fragment of SEQ ID NO. 5;

SEQ ID NO. 8 is a 22 base fragment of SEQ ID NO. 6;

SEQ ID NO. 9 is a 22 base fragment of SEQ ID NO. 5; and

SEQ ID NO. 10 is a 23 base fragment of SEQ ID NO. 6.

DETAILED DESCRIPTION OF THE INVENTION

We first determined the composition (DNA sequence) of the ITS 1 region of rRNA genes of *H. capsulatum* and found the nucleotide sequence to be unique to *H. capsulatum*. We then used the nucleotide sequence to design a PCR method which allows specific detection and identification of *H. capsulatum*.

The double-stranded ITS 1 DNA sequence is in lower case letters as follows:

```
AAGCTGGTCA AACTTGGTCA TTTAgaggaa gtaaaagtcg taacaaggtt  50
TTCGACCAGT TTGAACCAGT AAATctcctt cattttcagc attgttccaa tccgtagtga acctgcggaa ggatcattac cacgccgtggg ggctgggag 100
aggcatcact tggacgcctt cctagtaatg gtgcggcaccc ccgaccctc ctctgaccgg gacccgccct ctacccggcc accottgtct accggccacc 150
gagactggcc ctgggcggga gatgggccgg tgggaacaga tggccggtgg cttgtctacc ggacctgttg cctcggcggg ccctagcgat gctgcgggga 200
gaacagatgg cctggacaac ggagccgccc gggatcgcta cgacgcccct gcttctcccg ggccctggtc cgccggggac accgtaagaa ccgtcggtga 250
cgaagagggc ccgggaccag gcggcccctg tggcattctt ggcagccact acgattggcg tctgagcatg agagcgataa taatccagtc aAAACTTTCA 300
tgctaaccgc agactcgtac tctcgctatt attaggtcag tTTTGAAAGT

ACAACGGATC TA                                         312
TGTTGCCTAG AT
```

SEQ ID NO. 1 is double-stranded DNA from 25–291.

SEQ ID NO. 2 is 5' to 3' single-stranded DNA from 25–291.

SEQ ID NO. 3 is 3' to 5' single-stranded DNA from 25–291.

SEQ ID NO. 4 is double-stranded DNA from 66–254.

SEQ ID NO. 5 is 5' to 3' single-stranded DNA from 66–254.

SEQ ID NO. 6 is 3' to 5' single-stranded DNA from 66–254.

SEQ ID NO. 7 is 5' to 3' single-stranded DNA from 64–85.

SEQ ID NO. 8 is 3' to 5' single-stranded DNA from 257–278.

SEQ ID NO. 9 is 5' to 3' single-stranded DNA from 66–87.

SEQ ID NO. 10 is 3' to 5' single-stranded DNA from 232–254.

SEQ ID NOS. 7 and 8 are underlined in the sequence described above.

SEQ ID NOS. 9 and 10 are underlined in the copy of the ITS 1 sequence below:.

```
AAGCTGGTCA AACTTGGTCA TTTAgaggaa gtaaaagtcg taacaaggtt  50
TTCGACCAGT TTGAACCAGT AAATctcctt cattttcagc attgttccaa tccgtagtga acctgcggaa ggatcattac cacgccgtggg ggctgggag 100
aggcatcact tggacgcctt cctagtaatg gtgcggcaccc ccgaccctc ctctgaccgg gacccgccct ctacccggcc accottgtct accggccacc 150
gagactggcc ctgggcggga gatgggccgg tgggaacaga tggccggtgg cttgtctacc ggacctgttg cctcggcggg ccctagcgat gctgcgggga 200
gaacagatgg cctggacaac ggagccgccc gggatcgcta cgacgcccct gcttctcccg ggccctggtc cgccggggac accgtaagaa ccgtcggtga 250
cgaagagggc ccgggaccag gcggcccctg tggcattctt ggcagccact acgattggcg tctgagcatg agagcgataa taatccagtc aAAACTTTCA 300
tgctaaccgc agactcgtac tctcgctatt attaggtcag tTTTGAAAGT

ACAACGGATC TA                                         312
TGTTGCCTAG AT
```

Therefore, the present invention provides compounds which comprise DNA from SEQ ID NO. 1, SEQ ID. NO. 2, or SEQ ID NO. 3, or fragments thereof. Preferred embodiments of the present invention are the compounds which are SEQ ID NO. 4, SEQ ID NO. 5, SEQ ID NO. 6 or fragments thereof. Most preferred compounds are SEQ ID NO. 7, SEQ ID NO. 8, SEQ ID NO. 9, SEQ ID NO. 10 or fragments thereof.

Those in the art will recognize that certain conserved modification of the sequences identified in the present invention will not result in an alteration in function of the sequence. Moreover, it is likely that minor changes in the sequences of SEQ ID NOS. 7, 8, 9 and 10 described will result in amplification of the desired internal fragment. Those minor changes in sequences that artisans can predict will not change the function of the fragment are included in the scope of this invention.

Also provided by the present invention is a method for diagnosing H. capsulatum infection in a patient comprising the steps of harvesting: a biological sample from the patient; preparing the sample for PCR; conducting PCR using primers specific for SEQ ID NO. 4; electrophoresing the end product; and ascertaining the presence or absence of the appropriately-sized amplified fragment. A method which utilizes SEQ ID NO. 7, SEQ ID NO. 8, SEQ ID NO. 9 and SEQ ID NO. 10 as the primers, and in which the resulting amplified fragment ascertained is 189 base pairs in size, is preferred.

The best mode for practicing the method described is in the detection of H. capsulatum in clinical specimens such as bronchoalveolar lavage (BAL), tissue biopsies, sera or paraffin-embedded tissues. DNA is isolated from specimens containing H. capsulatum and used as templates for the PCR. This amplification process converts DNA from 2 copies to millions of copies, thus increasing the copy number of the target of diagnosis. The PCR products are then electrophoresed on a 6% polyacrylamide gel. After electrophoresis, the gel is stained with ethidium bromide and examined for the presence of a 189-bp band. The presence of this 189-bp band indicates the presence of *H. capsulatum* in a specimen.

Also provided by the present invention is a kit for use in diagnosing *H. capsulatum* infection in patients, comprising starting materials necessary for PCR; and primers consisting of SEQ ID NOS. 7 and 8, and SEQ ID NOS. 9 and 10. Preferred is a kit of claim 11, wherein the primers used are SEQ ID NO. 7 and SEQ ID NO. 8.

Lastly, those in the art recognize, however, that the sequences disclosed in the present application have a variety of uses; for example, as materials by which to accomplish the procedure set out by Bowman, B. H., *Clinical Immunology Newsletter,* 12:65–69 (1992). Those uses are contemplated as within the scope of the present invention.

As a means for clarifying the invention, and not by way of limitation, the following examples are given.

EXAMPLES

Example 1: Amplification of ITS 1 From rRNA Genes of *H. capsulatum*

To determine whether the nucleotide sequence of the ITS 1 region of the rRNA genes of *H. capsulatum* is unique, the ITS 1 region was amplified, cloned and sequenced. The rRNA genes are genes that are responsible for the production of various species of rRNAs including 18S, 5.8S, and 26S rRNAs. Amplification of the ITS1 region was achieved by using oligonucleotide primers 1724F (5'-AAGCTGGTCAAACTTGGTC-3') SEQ ID NO 11
5.8R ( 5 'AGATCCGTTGTTGAAAGTTT-3') SEQ ID NO 12.

Primer 1724F anneals to a 3' portion of the 18S rRNA gene, and primer 5.8R anneals to the 5.8S rRNA gene.

With the use of this pair of primers, the region located between the two primer binding simms was amplified. This region included 24 bp of the 3' portion of the 18S rRNA gene, the entire ITS1 (267 bp), and 21 bp of the 5' portion of the 5.8S rRNA gene. DNA isolated from *H. capsulatum* organisms was used as the template. Both yeast and mycelial forms of the organism were used. The organisms obtained from culture were pelleted by centrifugation in an Eppendorf centrifuge for 5 minutes and resuspended in 500 μl of proteinase K buffer (50 mM KCl; 15 mM Tris-HCl, pH 8.3; and 0.5% NP-40) containing 500 μg/ml proteinase K. After incubation at 37° C. overnight, the mixture was extracted with phenol and chloroform. The DNA in the aqueous phase was precipitated with ethanol, the ethanol was removed by vacuum drying and the DNA was dissolved in 50 μl of TE (10 mM Tris-HCl, pH 8.0; 1 mM EDTA). Ten μl of this solution was used for PCR. The PCR was performed in a 100 μl mixture containing template DNA, PCR buffer (10 mM Tris-HCl, pH 8.3; 50 mM KCl; 2 mM $MgCl_2$; 0.001% gelatin), 20 pmol of each PCR primer (1724F and 5.8R), 0.2 mM of each dNTP, and 2U of TaqI DNA polymerase. The mixture was overlaid with 100 μl of mineral oil to prevent evaporation during thermal cycling. PCR was performed in two stages. The initial stage was 30 cycles of 94° C., 1 min; 55° C., 2 min; 72° C., 2 min. The final stage was a 10 min extension at 72° C. The PCR products were electrophoresed in a 6% polyacrylamide gel and a 312 bp band was seen.

Example 2: Cloning of the PCR Product

The PCR product was purified using the Promega Magic PCR Prep kit (Promega, Madison, Wis.). The 312-bp PCR product was isolated from a low melting point agarose gel after electrophoresis. The gel slice containing the 312-bp band was placed in a tube and then heated to 70° C. to melt the agarose. The molten agarose was mixed with 1 ml of the Magic PCR Prep DNA purification resin. This agarose-resin mixture was pushed into a PCR column with a syringe and then washed with 2 ml of 80% isopropanol. After removing the isopropanol by centrifugation, DNA was eluted from the PCR column with 20 μl of warm (70° C.) water.

The purified PCR product was ligated with 50 ng of the TA cloning vector pCRII (Invitrogen, San Diego, Calif.). The ligated DNA was then introduced into *E. coli* strain INValphaF cells by transformation, and the transformants were plated on LB agar plates containing 100 μg/ml ampicillin, 0.5 μg/ml IPTG, and 2.5 μg/ml X-gal. Plasmid DNA from 12 colorless colonies was isolated, digested with EcoRI, and examined for the presence of a 312-bp band. Plasmid DNA from 7 of the 12 selected colonies contained the expected 312-bp band. The nucleotide sequences of the 312-bp inserts in these plasmids were then determined.

Example 3: Sequencing

Nucleotide sequencing was performed using the Sequenase kit (Version 2) obtained from USB (Cleveland, Ohio). Primers (−40: 5'-GTTTTCCCAGTCACGAC-3' SEQ ID NO. 13 and Reverse: (5'AGCGGATAACAATTTCACACAGGA-3') SEQ ID NO. 14 that anneal to regions on the vector flanking the inserts were used. Approximately 2.5 μg of plasmid which contains the 312-bp insert was mixed with 1 μl (0.3 ng) of sequencing primer and 1 μl of 0.5N NaOH. The mixture was heated at 80° C. for 5 minutes to denature the plasmid DNA and then allowed to cool slowly to room temperature. One μl of a 0.5N HCl solution was added to neutralize the mixture. This mixture was combined with 2 μl of a 5× sequencing buffer (200 mM Tris-HCl, pH 7.5; 100 mM $MgCl_2$; 250 mM NaCl), 1 μl of 0.1M DTT, 2 μl of labeling mix (1.5 μM each of dGTP, dCTP, and dTTP), 1 μl (10 uCi) of alpha-$^{35}$S-dATP, and 2 μl (2 units) of Sequenase and then incubated at room temperature for 5 minutes. The reaction mixture was then divided into 4 aliquots (3.5 μl each). Each aliquot was mixed in each of the tubes labelled G, A, T, or C containing 2.5 μl each of ddGTP (80 μM each dNTP, 80 μM ddGTP, and 50 mM NaCl), ddATP (80 μM each dNTP, 80 μM ddATP, and 50 mM NaCl), ddTTP (80 μM each dNTP, 80 μM ddTTP and 50 mM NaCl), and ddCTP (80 μM each dNTP, 80 μM ddCTP, and 50 mM NaCl), respectively. After 10 minutes incubation at 37° C., 4 μl of sequencing dye (80% formamide, 10 mM NaOH, 1 mM EDTA, 0.1% xylene cyanol, 0.1% bromophenol blue) was added to each tube. The tubes were heated at 80° C. for 2 minutes and then chilled on ice. Two μl of the sample in each tube was electrophoresed in a DNA sequencing gel.

Example 4: Analysis of Nucleotide Sequence

The following sequence was obtained:

```
AAGCTGGTCA AACTTGGTCA TTTAgaggaa gtaaaagtcg taacaaggtt 50
TTCGACCAGT TTGAACCAGT AAATctcctt cattttcagc attgttccaa
```

```
tccgtagtga  acctgcggaa  ggatcattac  cacgccgtggg  ggctgggag  100
aggcatcact  tggacgcctt  cctagtaatg  gtgcggcaccc  ccgaccctc ctctgaccgg  gacccgccct  ctacccggcc  acccttgtct  accggccacc  150
gagactggcc  ctgggcggga  gatgggccgg  tgggaacaga  tggccggtgg cttgtctacc  ggacctgttg  cctcggcggg  ccctagcgat  gctgcgggga  200
gaacagatgg  cctggacaac  ggagccgccc  gggatcgcta  cgacgcccct gcttctcccg  ggccctggtc  cgccggggac  accgtaagaa  ccgtcggtga  250
cgaagagggc  ccggggaccag  gcggcccctg  tggcattctt  ggcagccact acgattggcg  tctgagcatg  agagcgataa  taatccagtc  aAAACTTTCA  300
tgctaaccgc  agactcgtac  tctcgctatt  attaggtcag  tTTTGAAAGT

ACAACGGATC TA                                              312
TGTTGCCTAG AT
```

This is the nucleotide sequence of the 312-bp PCR product (SEQ ID NO: 2) amplified from *H. capsulatum*. The area printed with lower case letters is the ITS 1 region.

The composition of this sequence was analyzed by comparing it with the sequences in the Genbank using the PC Gene Programs (IntelliGenetics, Mountain View, Calif.). This analysis revealed that the first 24 bps, the next 267 bps, and the last 21 bps belong to the 18S rRNA gene, the ITS1, and the 5.8S rRNA gene, respectively. The ITS1 sequence was further examined for its similarity to other sequences and was found to be unique to *H. capsulatum*.

Example 5: Design of PCR Primers

The ITS1 sequence was then used to develop a PCR specific for *H. capsulatum*. The sequence was examined for areas that best fit the criteria for PCR primers. Two sets of primers (Histo-F1/Histo-RI and Histo-F2/Histo-R2) were selected. The sequences of these primers are

| | | |
|---|---|---|
| Histo-F1: | 5'-TGCGGAAGGATCATTACCACGC-3', | (SEQ ID. NO:7) |
| Histo-R1: | 5'-ATCGCTCTCATGCTCAGACGCC-3', | (SEQ ID. NO:8) |
| Histo-F2: | 5'-CGGAAGGATCATTACCACGCCG-3', | (SEQ ID. NO:9) |
| Histo-R2: | 5'-TCGTTCACCGACGGTTCTTACGG-3'. | (SEQ ID. NO:10) |

These two sets of primers allow the performance of a nested PCR. The first PCR amplifies a 215-bp region (nucleotide positions 64–278) within the ITS1. The second PCR amplifies the region between nucleotide positions 66–254 (189-bp).

Example 6: Determination of Specificity

To determine the specificity of these two sets of primers, PCRs were run on DNA isolated from several different fungi including *H. capsulatum, Saccharomyces cerevisiae, Candida albicans, Cryptococcus neoformans, Blastomyces dermatitidis* and *Aspergillus fumigatus* that are commonly seen in clinical specimens. The first PCR was performed with primers Histo-F1 and Histo-F2 (30 pmoles each) in a 100 µl mixture containing 100 ng of template DNA, PCR buffer (10 mM Tris-HCl, pH 8.3; 50 mM KCl; 2 mM $MgCl_2$; 0.001% gelatin), 0.2 mM of each dNTP, and 2U of TaqI DNA polymerase. The mixture was overlaid with 100 µl of mineral oil to prevent evaporation during thermal cycling. PCR was performed in three stages. The initial stage was a 10-minute denaturation at 94° C. The second stage was 30 cycles of 94° C., 1 min.; 55° C., 2 min.; 72° C., 2 min. The final stage was a 10-minute extension at 72° C.

After the completion of the fn:st PCR, 1 µl of the reaction mixture was used as the template for the second PCR. The second PCR mixture contained, in addition to the 1 µl of the first PCR reaction mixture, PCR buffer (10 mM Tris-HCl, pH 8.3; 50 mM KCl; 2 mM $MgCl_2$; 0.001% gelatin), 30 pmoles of each primer (Histo-F2 and Histo-R2), 0.2 mM of each dNTP, and 2U of TaqI DNA polymerase. The second PCR was also performed in 3 stages. The initial stage was a 10 min. denaturation at 94° C. The second stage was 35 cycles of 94° C., 1 min; 60° C., 2 min; 72° C., 2 min. The final stage was a 10 min extension at 72° C. After the reaction, 10 µl of the second PCR reaction mixture was electrophoresed on a 6 % polyacrylamide gel.

A 189-bp band was seen in the lane containing PCR products amplified from *H. capsulatum* DNA. Significantly, this 189-bp band was not seen in lanes containing PCR products amplified from *Saccharomyces cerevisiae, Candida albicans, Cryptococcus neoformans, Blastomyces dermatitidis* and *Aspergillus fumigatus*. These results indicate that this nested PCR is specific to *H. capsulatum*. This nested PCR was designated Histo-ITS-PCR.

Example 7: Detection and Identification of *H. capsulatum* in Clinical Specimens To determine whether the Histo-ITS-PCR can be used to diagnose *H. capsulatum* infections, it was run on specimens that are commonly used for diagnosis including bronchoalveolar lavage (BAL), biopsies, paraffin-embedded tissues and sera. These specimens were processed for the Histo-ITS-PCR as follows. For BAL specimens, the organisms present in BAL were pelleted by centrifugation in an Eppendorf centrifuge for 5 minutes and resuspended in 500 µl of proteinase K buffer (50 mM KCl; 15 mM Tris-HCl, pH 8.3; and 0.5% NP-40) containing 500 µg/ml proteinase K. For tissue specimens, a portion weighing approximately 0.5 mg was homogenized in proteinase K buffer. Proteinase K was then added to a final concentration of 500 µg/ml.

To use paraffin-embedded tissues, a 15 µm section of the embedded tissue was cut and placed onto the center of a 30 circular glass fiber filter (0.7 cm in diameter) which was lying on a pad of paper towels. A drop of xylene was dripped onto the tissue to remove most of the paraffin. This tissue-filter unit was soaked in 0.5 ml of xylene at room temperature for 5 minutes. After removing the xylene, the tissue-filter unit was washed with 100% ethanol two times. The ethanol was then removed under vacuum and the tissue-filter unit was digested with proteinase K (500 µg/ml) in 100 µl of K-buffer (50 mM KCl, 15 mM Tris-HCl pH 8.3, 0.5% NP-40) at 37° C. overnight. To use serum specimens for PCR, 20 µl of serum was digested with proteinase K (500 µg/ml) in 100 µl of proteinase K buffer at 37° C. overnight.

After the proteinase K digestion, the reaction mixture was boiled in a water bath for 10 minutes. The mixture was then clarified by centrifuging the tubes at 14,000 rpm at 4° C. for 5 minutes in an Eppendorf centrifuge, and the clarified supernatant was extracted with phenol and chloroform. The DNA in the aqueous phase was precipitated with ethanol, the ethanol was removed by vacuum drying, and the DNA was dissolved in 50 µl of TE (10 mM Tris-HCl, pH 8.0; 1 mM EDTA). Ten µl of this solution was used for the Histo-ITS-PCR which was performed as described above. The results of this study are summarized below.

A total of 118 specimens, including 52 BALs, 2 fresh tissue biopsies, 31 sera, 23 paraffin embedded tissues and 10 H. capsulatum isolates, were examined by the Histo-ITS-PCR. All the BAL and fresh tissue specimens were also examined by culture and microscopy for bacteria, viruses and fungi. Serum specimens from most patients were assayed for the presence of H. capsulatum antigens by the method of Wheat et al.; those from volunteers were not assayed for H. capsulatum antigens. Paraffin-embedded tissues from patients with granuloma were examined by microscopy for pathological changes of the tissue and the presence of bacteria or fungi in the tissue. Serum specimens from these granuloma patients were examined for the presence of antibodies against H. capsulatum (serology).

Twenty-seven of the 52 BAL specimens were obtained from patients that were diagnosed with histoplasmosis. All of these 27 BAL specimens were Histo-ITS-PCR positive for the Histo-ITS-PCR. None of the BAL specimens from patients with unknown etiology or with an etiology other than H. capsulatum (bacteria, viruses or other fungi) was positive for the Histo-ITS-PCR. One of the fresh tissue specimens from a patient with histoplasmosis was positive for the Histo-ITS-PCR. Eight of the 31 serum specimens from patients with histoplasmosis were positive for the Histo-ITS-PCR. Among the 23 paraffin-embedded tissues examined, 13 of them were positive for the Histo-ITS-PCR. These 13 specimens were confirmed by microscopy and serology to be from patients with histoplasmosis. All 10 H. capsulatum isolates were Histo-ITS-PCR positive.

These results indicate that the Histo-ITS-PCR is effective in detecting H. capsulatum DNA from a wide variety of clinical specimens. It has a specificity of 100 % since it did not produce a positive reaction on specimens that do not contain H. capsulatum. In addition, the Histo-ITS-PCR results agreed completely with those of other diagnostic methods for histoplasmosis, suggesting that the Histo-ITS-PCR has a sensitivity of 100%. The fact that all 10 different H. capsulatum isolates were positive for the Histo-ITS-PCR suggests that the Histo-ITS-PCR can detect all H. capsulatum strains.

What is claimed is:

1. A compound which comprises isolated DNA chosen from the group consisting of SEQ ID NO: 1, SEQ ID NO: 2, SEQ ID NO: 3 or a fragment thereof which specifically hybridizes Histoplasma capsulatum nucleic acids.

2. A compound of claim 1, which is SEQ ID NO: 4, or a fragment thereof which specifically hybridizes Histoplasma capsulatum nucleic acids.

3. A compound of claim 1, which is SEQ ID NO: 5, or a fragment thereof which specifically hybridizes Histoplasma capsulatum nucleic acids.

4. A compound of claim 1, which is SEQ ID NO: 6, or a fragment thereof which specifically hybridizes Histoplasma capsulatum nucleic acids.

5. A compound of claim 3, which is SEQ ID NO: 7, or a fragment thereof which specifically hybridizes Histoplasma capsulatum nucleic acids.

6. A compound of claim 4, which is SEQ ID NO: 8, or a fragment thereof which specifically hybridizes Histoplasma capsulatum nucleic acids.

7. A compound of claim 3, which is SEQ ID NO: 9, or a fragment thereof which specifically hybridizes Histoplasma capsulatum nucleic acids.

8. A compound of claim 4, which is SEQ ID NO: 10, or a fragment thereof which specifically hybridizes Histoplasma capsulatum nucleic acids.

9. A method for diagnosing Histoplasma capsulatum infection in a patient comprising:

obtaining a blood sample from the patient;

preparing the blood sample for PCR;

conducting PCR using primers which specifically hybridize to SEQ ID NO: 4 so as to generate an end product containing a plurality of fragments which are distinguishable by electrophoresis as amplified by Histoplasma capsulatum sequences in the event that the blood sample contains Histoplasma capsulatum;

electrophoresing the end product; and ascertaining the presence or absence of the plurality of fragments.

10. The method of claim 9, wherein the primers used are SEQ ID NO: 7 and SEQ ID NO: 8.

11. The method of claim 9, wherein the primers used are SEQ ID NO: 9 and SEQ ID NO: 10.

12. A kit for use in diagnosing Histoplasma capsulatum infection in patients, comprising: starting materials necessary for PCR; and primers consisting of SEQ ID NO: 7 and SEQ ID NO:8, and SEQ ID NO: 9 and SEQ ID NO: 10.

13. A kit of claim 12, wherein the primers used are SEQ ID NO: 7 and SEQ ID NO: 8.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 267 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAGGAAGTAA AAGTCGTAAC AAGGTTTCCG TAGTGAACCT GCGGAAGGAT CATTACCACG      60
CCGTGGGGGC TGGGAGCTCT GACCGGGACC CGCCCTCTAC CCGGCCACCC TTGTCTACCG     120
GCCACCCTTG TCTACCGGAC CTGTTGCCTC GGCGGGCCCT AGCGATGCTG CGGGGAGCTT     180
CTCCCGGGCC CTGGTCCGCC GGGGACACCG TAAGAACCGT CGGTGAACGA TTGGCGTCTG     240
AGCATGAGAG CGATAATAAT CCAGTCA                                        267
```

( 2 ) INFORMATION FOR SEQ ID NO:2:

( i ) SEQUENCE CHARACTERISTICS:
        ( A ) LENGTH: 312 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
AAGCTGGTCA AACTTGGTCA TTTAGAGGAA GTAAAAGTCG TAACAAGGTT TCCGTAGTGA      60
ACCTGCGGAA GGATCATTAC CACGCCGTGG GGGCTGGGAG CTCTGACCGG GACCCGCCCT     120
CTACCCGGCC ACCCTTGTCT ACCGGCCACC CTTGTCTACC GGACCTGTTG CCTCGGCGGG     180
CCCTAGCGAT GCTGCGGGGA GCTTCTCCCG GGCCCTGGTC CGCCGGGGAC ACCGTAAGAA     240
CCGTCGGTGA ACGATTGGCG TCTGAGCATG AGAGCGATAA TAATCCAGTC AAAACTTTCA     300
ACAACGGATC TA                                                        312
```

( 2 ) INFORMATION FOR SEQ ID NO:3:

( i ) SEQUENCE CHARACTERISTICS:
        ( A ) LENGTH: 267 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
TGACTGGATT ATTATCGCTC TCATGCTCAG ACGCCAATCG TTCACCGACG GTTCTTACGG      60
TGTCCCCGGC GGACCAGGGC CCGGGAGAAG CTCCCCGCAG CATCGCTAGG GCCCGCCGAG     120
GCAACAGGTC CGGTAGACAA GGGTGGCCGG TAGACAAGGG TGGCCGGGTA GAGGGCGGGT     180
CCCGGTCAGA GCTCCCAGCC CCACGGCGT GGTAATGATC CTTCCGCAGG TTCACTACGG      240
AAACCTTGTT ACGACTTTTA CTTCCTC                                        267
```

( 2 ) INFORMATION FOR SEQ ID NO:4:

( i ) SEQUENCE CHARACTERISTICS:
        ( A ) LENGTH: 189 base pairs
        ( B ) TYPE: nucleic acid (C) STRANDEDNESS: double
(D) TOPOLOGY: linear (i i) MOLECULE TYPE: DNA (genomic)

(x i) SEQUENCE DESCRIPTION: SEQ ID NO:4:

```
CGGAAGGATC ATTACCACGC CGTGGGGGCT GGGAGCTCTG ACCGGGACCC GCCCTCTACC      60
CGGCCACCCT TGTCTACCGG CCACCCTTGT CTACCGGACC TGTTGCCTCG GCGGGCCCTA     120
GCGATGCTGC GGGGAGCTTC TCCCGGGCCC TGGTCCGCCG GGACACCGT AAGAACCGTC      180
GGTGAACGA                                                             189
```

(2) INFORMATION FOR SEQ ID NO:5:

(i) SEQUENCE CHARACTERISTICS:
(A) LENGTH: 189 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:5:

```
CGGAAGGATC ATTACCACGC CGTGGGGGCT GGGAGCTCTG ACCGGGACCC GCCCTCTACC      60
CGGCCACCCT TGTCTACCGG CCACCCTTGT CTACCGGACC TGTTGCCTCG GCGGGCCCTA     120
GCGATGCTGC GGGGAGCTTC TCCCGGGCCC TGGTCCGCCG GGACACCGT AAGAACCGTC      180
GGTGAACGA                                                             189
```

(2) INFORMATION FOR SEQ ID NO:6:

(i) SEQUENCE CHARACTERISTICS:
(A) LENGTH: 189 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:6:

```
TCGTTCACCG ACGGTTCTTA CGGTGTCCCC GGCGGACCAG GGCCCGGGAG AAGCTCCCCG      60
CAGCATCGCT AGGGCCCGCC GAGGCAACAG GTCCGGTAGA CAAGGGTGGC CGGTAGACAA     120
GGGTGGCCGG GTAGAGGGCG GGTCCCGGTC AGAGCTCCCA GCCCCACGG CGTGGTAATG      180
ATCCTTCCG                                                             189
```

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

```
TGCGGAAGGA TCATTACCAC GC                                               22
```

(2) INFORMATION FOR SEQ ID NO:8:

(i) SEQUENCE CHARACTERISTICS:
(A) LENGTH: 22 base pairs
(B) TYPE: nucleic acid
(C) STRANDEDNESS: single
(D) TOPOLOGY: linear (  i  i  )  MOLECULE TYPE: DNA (genomic)

(  x  i  )  SEQUENCE DESCRIPTION: SEQ ID NO:8:

ATCGCTCTCA TGCTCAGACG CC    22

( 2 ) INFORMATION FOR SEQ ID NO:9:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CGGAAGGATC ATTACCACGC CG    22

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

TCGTTCACCG ACGGTTCTTA CGG    23

( 2 ) INFORMATION FOR SEQ ID NO:11:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:11:

AAGCTGGTCA AACTTGGTC    19

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:12:

AGATCCGTTG TTGAAAGTTT    20

( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:13:

```
GTTTTCCCAG TCACGAC                                                    17
```

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:14:

```
AGCGGATAAC AATTTCACAC AGGA                                            24
```

\* \* \* \* \*